Figure 1:
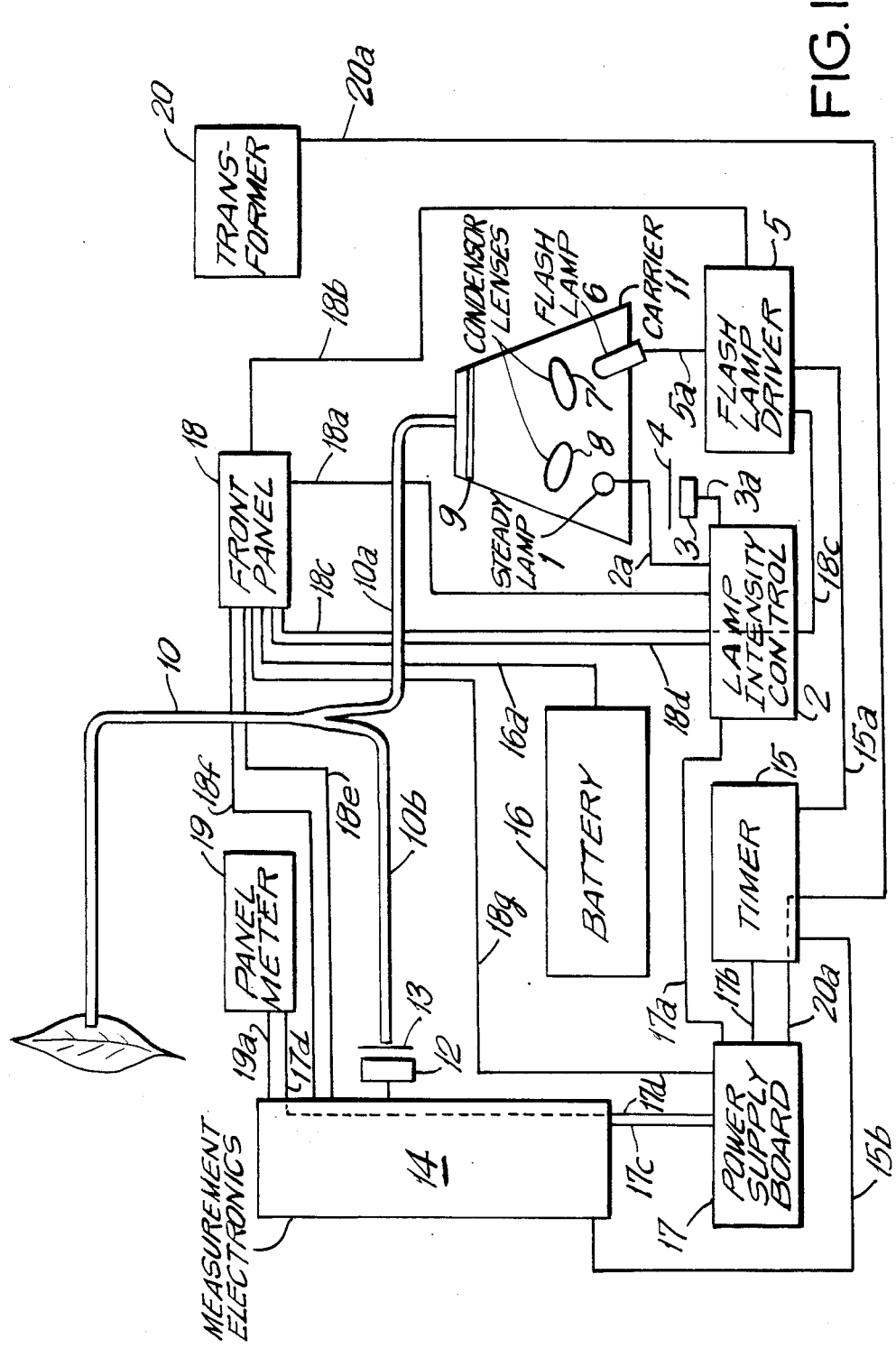

United States Patent [19]

Moll

[11] Patent Number: 4,650,336

[45] Date of Patent: Mar. 17, 1987

[54] MEASUREMENT OF VARIABLE FLUORESCENCE OF PLANTS

[75] Inventor: Benjamin A. Moll, Berkeley, Calif.

[73] Assignee: Advanced Genetic Sciences, Inc., Oakland, Calif.

[21] Appl. No.: 778,497

[22] Filed: Sep. 20, 1985

[51] Int. Cl.⁴ .............................................. G01J 3/50
[52] U.S. Cl. ..................................... 356/417; 356/317; 250/458.1
[58] Field of Search ................ 356/311, 317, 318, 417; 434/295; 250/458.1, 461.2, 461.1

[56] References Cited

U.S. PATENT DOCUMENTS 1,076,786  10/1913  Reinherz .......................... 434/295 X
4,461,619   7/1984  Hendry et al. ....................... 434/295
4,533,246   8/1985  Braun ................................... 356/317

OTHER PUBLICATIONS

A. R. Crofts et al., *Biochimica et Biophysica Acta*, 726, 149–85, (1983), "The Electrochemical Domain of Photosynthesis".
D. C. Fork et al., *Carnegie Inst. Washington Yearbook*, 81, 52–57, (1980); "Photoinhibition in Bean: A Fluorescence Analysis".
P. Poulet et al., *Biochimica et Biophysica Acta*, 724, 433–46, (1983); "Photoacoustic Detection of Photosynthetic Oxygen Evolution From Leaves".
G. Papageorgiou, *Bioenergetics of Photosynthesis*, (Gorindjee, ed.) Chap. 6, 319–71, (1975); "Chlorophyll Fluorescence: An Intrinsic Probe of Photosynthesis".
N. Baker et al, *J. Exptl. Botany*, 34, 189–97, (1983); "Chilling Damage to Photosynthesis in Young Zea mays".
M. Havaux et al., *Photosynthetica*, 18, 117–27, (1984); "Effects of Chilling Temperatures On Prompt and Delayed Chlorophyll Fluorescence In Maize and Barley Leaves".
Brochure entitled "Plant Productivity Fluorometer Model SF-10" (Richard Brancker Research Ltd.).
Brochure entitled "Plant Productivity Fluorometer Model SF-20" (Richard Brancker Research Ltd.).
N. Baker et al., *Plants and Daylight Spectrum*, (H. Smith, ed.), 355–73, (1981); "Possible Applications of Chlorophyll Fluorescence Techniques for Studying Photosynthesis In vivo".
R. M. Smillie et al., *Plant Physiol.*, 72, 1043–50, (1983), "Stress Tolerance and Stress–Induced Injury In Crop Plants Measured by Chlorophyll Fluorescence In vivo".
S. E. Heatherington et al, *Aust. J. Plant. Physiol.*, 9, 587–99, (1982); "Humidity–Sensitive Degreening and Regreening of Leaves of Boyra nitida Labilli as followed by changes in Chlorophyll Fluor.".
J. M. Bowes et al, *Biochimica et Biophysica Acta*, 590, 373–84, (1980); "Binary Oscillations in the Rate of Reoxidation of the Primary Acceptor of Photosystem II".
J. A. Van Best et al., *Biochimica et Biophysica Acta*, 590, 373–84, (1975); "Reactions Between Primary and Secondary Acceptors of Photosystem II In Chlorella Pyrenoidosa Under Anaerous Conditions as Studied by Chlorophyll a Fluroescence".

*Primary Examiner*—Eugene R. LaRoche
*Assistant Examiner*—David Mis
*Attorney, Agent, or Firm*—Davis Hoxie Faithfull & Hapgood

[57] ABSTRACT

A method of testing a plant to determine the variable fluorescence of the plant, and instrumentation for carrying out the method, is described. The method has use in determining the extent to which a plant has been damaged by photoinhibitory stress, or is susceptible to damage by such stress.

23 Claims, 1 Drawing Figure

MEASUREMENT OF VARIABLE FLUORESCENCE OF PLANTS

This invention relates to determination of variable fluorescence and to testing of a plant to determine the extent to which the plant has been damaged by stress. In particular, this invention relates to fluorescence analysis of a plant to determine damage from stress which can inhibit the photosynthetic apparatus of the plant.

Photosynthesis is the process by which green plants absorb light energy from sunlight and use that energy to produce sugar from carbon dioxide and water. The process involves a complex series of chemical reactions which take place within plant cell chloroplasts. One group of reactions, the "light reactions", requires the presence of sunlight. The light reactions serve to produce high energy compounds (ATP and NADPH). A second group of reactions, the "dark reactions", can take place in the dark and serves to convert $CO_2$ to sugar using energy supplied by the high energy compounds ($CO_2$ fixation).

The light reactions include a series of electron transfer reactions and involve two chemical complexes, or reaction centers, known as Photosystem II (PS II) and Photosystem I (PS I). The reaction centers contain chlorophyll molecules (chlorophyll a and chlorophyll b), proteins, enzymes, carotenoids, pigments and lipids. In the light reactions, light energy is transferred to a chemically active pigment $P_{680}$. This energy is transferred to an electron, which is then donated to a series of electron carriers, including the plastoquinone carriers $Q_A$ and $Q_B$. The electron lost from $P_{680}$ is replaced by the oxidation of water, releasing one $O_2$ molecule per four electrons transferred. The electron from PS II is subsequently transferred, via plastoquinone PQ and subsequent carriers, to PS I and beyond, eventually yielding the high energy compounds. As stated, the high energy compounds are employed in the $CO_2$ fixation process of the dark reactions. See, in general, A. R. Crofts et al., *Biochimica et Biophysica Acta,* 726, 149–85 (1983) regarding the electron transfer process.

Many forms of plant stress are associated with damage to, or inhibition of, the photosynthetic system. Such forms of stress include chilling (0°–15° C.), high temperature, high light intensity, carbon dioxide depletion, drought stress, anaerobic stress, ozone stress, salinity stress and sulphur dioxide stress. Certain herbicides which interact with the photosynthetic system also cause damage, e.g., ureas such as diuron; s-triazines such as atrazine; amides such as propanil; benzothiodiazanones such as bentazon; carbamates such as Swep; nitrophenols such as dinoseb; nitriles such as ioxynil; pyridazanones such as pyrazon; thiodazoles such as buthidazole; triazinones such as metribuzin; and uracils such as bromacil. Damage caused by such stresses shall be referred to herein as photoinhibitory damage. Photoinhibition is the light-dependent loss of photosynthetic electron transport capacity. Herbicides causing photoinhibitory damage shall be referred to herein as photoinhibitory herbicides. Stress causing such damage shall be referred to herein as photoinhibitory stress.

Chill stress is a particular problem for a wide variety of plants, e.g., rice, corn, soybean, cotton and other crops of tropical origin. For many of these plants, in particular for chill-sensitive varieties, a major adverse effect of chill is damage to the photosynthesis system.

The basis of photoinhibitory damage is disruption of the electron transfer chain in the light reactions. Specifically, the damage caused by photoinhibitory stress slows or halts the movement of electrons from PS II to PS I due to inactivation, partial or full, of the PS II reaction center. Exposure to stress conditions in the presence of light lowers the characteristic PS II fluorescence emission yield, a measure of photosynthetic activity. This is disclosed in D. C. Fork et al., *Carnegie Inst. Washington Yearbook,* 81, 52–57 (1980), (hereinafter "Fork") along with possible explanations for the phenomenon.

Because of the adverse effect which stress can have on a plant, it is important to be able to determine whether a plant which has been exposed to a stress has been damaged by it. It is also important to be able determine whether a plant which has not been exposed to a stress is sensitive to the stress (i.e., susceptible to damage caused by the stress) or whether the particular plant is resistant to the stress. Several approaches to monitoring the effect of plant stress have been tried in the past, that is, approaches to monitoring the functionality of the plant photosynthetic system and, specifically, the PS II reaction center. As used herein, the term functionality means the extent to which the plant or its photosynthetic system is functioning like a normal, non-stress damaged, in vivo system.

One approach is to expose the plant to a given stress and then, after removal of the stress, assess the health of the plant from the whole plant perspective. Thus, in the case of chill stress, the plant can be chilled and then examined at some point after removal of the chill to see if the plant dies or shows visible signs of damage. In a more refined manner, the health of the plant can be assayed based on physiological performance, e.g., $CO_2$ uptake capacity or $O_2$ evolution. Instruments are available commercially for such measurements, e.g., the LI-COR model LI-6000 Portable Photosynthesis System (manufactured by LI-COR, Inc. of Lincoln, Nebraska) which can be used to measure apparent plant photosynthesis based on gas exchange. The use of this instrument is explained in a brochure distributed by the manufacturer entitled "The LI-6000 Portable Photosynthesis System".

Another approach to measuring photosynthetic activity involves photoacoustic techniques. The method calls for illumination of a plant with an audio frequency modulated light source. A microphone is used to measure an audio signal received from the plant which contains components arising from heating of the internal air spaces and arising from internal pressure increases due to oxygen release. Heating results from conversion of light to heat. The extent of heating depends on the proportion of light energy converted to heat energy, as opposed to chemical energy; the greater the conversion to chemical energy the less the heat and thus the lower the audio signal. Measurements made in this manner are not PSII-specific and their interpretation is complex. P. Poulet et al., *Biochmica et Biophysica Acta,* 724, 433–46 (1983).

Other approaches involve the use of fluorescence as a probe of photosynthetic activity in green plants, see, in general, G. Papageorgiou, *Bioenergetics of Photosynthesis,* (Gouindjee, ed.) Chap. 6, 319–71 (1975) for background on this subject. Specifically, the phenomenon of variable fluorescence ($F_v$) has been used in this regard. Variable fluorescence is the increase in fluorescence (incremental fluorescence) arising from PS II when the first stable electron acceptor of PS II, $Q_A$, is reduced instead of oxidized. Variable fluorescence is a measure of total electron transport capacity within PS II and has been found to correlate directly with the functionality of the photosynthetic system. $F_v$ will be relatively large for a plant with a properly functioning photosynthetic system. In the event of application of any one of a variety of stress regimes leading to damage to PS II, $F_v$ will be reduced proportionately. The extent of reduction will depend on the extent of damage. This is disclosed in Fork, wherein at page 52 it is explained that loss of PS II fluorescence is associated with photoinhibition of photosynthesis. By comparing the variable fluorescence of a sample plant to that of a control, the extent of stress damage experienced by the sample plant can be determined.

One way to measure variable fluorescence is a method which shall be referred to herein as the electron-blocked variable fluorescence method. This method calls for measuring the fluorescence increase upon illumination of a dark-adapted, electron transfer-blocked plant. A plant part with electron transport blocked is dark adapted. The plant part can be a specific part of a plant (e.g., a leaf) or a preparation derived from a plant (e.g., a thylakoid preparation). This normally takes place over a period of minutes or hours. Electron transport can be blocked in various ways, for instance, by extreme low temperatures, e.g., 77° K., or by treatment with a chemical which blocks electron transport beyond $Q_A$, e.g., herbicides such as diuron (3-(3,4-dichlorophenyl)-1,1-dimethyl urea) or atrazine. Treatment with extreme low temperature or with electron blocking chemicals shall be referred to herein as electron transport blocking conditions. Upon exposure of the plant part or preparation to a continuous (steady) source of visible light, fluorescence (685 nm) is at first at a low level ($F_o$) and subsequently rises to a maximum level ($F_{max}$). Under these conditions the difference between $F_{max}$ and $F_o$, that is, the increase in fluorescence, is the variable fluorescence (i.e., the "electron blocked variable fluorescence"). $F_{max}$ is associated with the electron carrier $Q_A$ being in its reduced state, a state in which fluorescence is not quenched (in its oxidized state, fluorescence is quenched).

N. Baker et al., J. Exptl. Botany, 34, 189–97 (1983) discloses the use of an electron-blocked variable fluorescence method to assess chill damage in Zea mays. Based on tests of dark adapted plants with electron flow blocked by either diuron or very low temperature (77° K.), it was found that the effect of chill on fluorescence induction was to decrease the yield of PS II fluorescence.

A drawback of the electron-blocked variable fluorescence method is the need to dark adapt. Dark adaptation is time consuming and is best done under controlled conditions, e.g., in a growth chamber. Dark adaptation in the greenhouse or in the field is difficult or unworkable, particularly for larger numbers of plant samples. Another drawback is the need to block electron transport. This step involves sample handling and is again time consuming.

Another way to measure variable fluorescence is a method which shall be referred to herein as the Kautsky effect variable fluorescence method. The Kautsky effect is the increase in fluorescence upon illumination of a dark-adapted, non-electron transfer blocked plant. Because $CO_2$ fixation is turned off during the dark adaptation, electron transport is very slow upon commencement of illumination. Fluorescence increases during initial illumination, eventually reaching a peak level. The extent of increase provides a measure of how well the photosynthetic system is functioning.

M. Havaux et al., Photosynthetica, 18, 117–27 (1984) discloses a study of dark-adapted (for at least 20 minutes) leaves using the Kautsky effect variable fluorescence method (the Kautsky effect is characterized on page 118 as fluorescence induction of the plants) to monitor the effects of chilling in maize and barley.

N. Baker et al., Plants and the Daylight Spectrum, (H. Smith, ed.), 355–73 (1981) discloses a study of the redox state of the plastoquinone (PQ) pool in which a dark-adapted bean leaf was excited with an actinic light source to generate an induction curve ($F_{685}$ vs. time), and then at various time points on the curve additional radiation (of the same intensity as the initial radiation) was introduced. The fluorescence levels were correlated to the proportion of PQ in the oxidized state.

The Kautsky effect is the basis of a commercial device known as the Plant Productivity Fluorimeter, Model SF-10 or Model SF-20 (manufactured by Richard Brancker Research Ltd. of Ottawa, Canada). In the manufacturer's sales brochures for these models (entitled "Plant Productivity Fluorimeter Model SF-10" and "Plant Productivity Fluorimeter Model SF-20"), the Kautsky effect is referred to under the heading "Purpose and Description". The device is to provide a test for photosynthetic activity. The light source is a Sensing Probe containing an LED (light emitting diode) to provide continuous monochromatic illumination.

R. M. Smillie et al., Plant Physiol., 72, 1043–50 (1983) (hereinafter "Smillie") discloses use of the Brancker Model SF-10 fluorimeter on leaf material dark adapted before use. Smillie describes use of the fluorimeter to measure tolerance of various plants to chill and other stresses in terms of the maximal rate of induced fluorescence rise and the time to decrease by 50%. Smillie discloses that the kinetics of the induced fluorescence rise were recorded as described in S. E. Hetherington et al., Aust. J. Plant Physiol., 9, 587–99 (1982) (hereinafter "Hetherington"). Hetherington discloses a study of desiccation tolerance using fluorescence as a probe, in which there were measurements of "short-term or fast fluorescence measurements" lasting over a period of 10 seconds and long-term or slow 200 second readings.

The Kautsky effect variable fluorescence method has limitations. It requires dark adaptation, with attendant problems as discussed above. Also, time must be taken to allow each fluorescence reading to reach its peak value. In addition, this approach does not lend itself to taking readings on plant tissue culture samples.

There are also reports of the use of fluorescence as a means for basic study of the photosynthetic system of plants or lower photosynthetic life forms, apart from considerations of photoinhibition or plant stress damage. For example, J. M. Bowes et al., Biochimica et Biophysica Acta, 590, 373–84 (1980) discloses a study of kinetics, redox potentials and mechanism based on fluorescence measurements taken at varying times (50 microseconds–10 milliseconds) after saturating actinic laser flashes. J. A. Van Best et al., Biochimica et Biophysica Acta, 408, 154–63 (1975) discloses a study of kinetics and mechanism based on fluorescence measurements taken at intervals of 50 microseconds to several minutes after saturating actinic flashes (laser or Xenon flashes) under anaerobic conditions.

The invention is an improved method for measuring variable fluorescence of a plant. The invention is also a method for assessing the functionality of the photosynthetic apparatus of a plant and for assessing damage to the plant resulting from a stress episode (in particular, photoinhibitory stress). In addition, the invention is a method of testing a plant for susceptibility to stress damage. Variable fluorescence is measured as the difference between a low level, steady state fluorescence and the level of a fluorescent transient (i.e., the increase in fluorescence level is measured). In accordance with the method of the invention, a non-dark adapted, non-electron transport blocked plant is illuminated with a steady lamp (a lamp providing a constant level of illumination) and the level of the resulting steady state fluorescence is measured. The illuminated plant is then subjected to a flash of light from a flash lamp to bring about transient fluorescence, and the level of transient fluorescence is measured within approximately 500 usec (microsecond) of the flash start point. The measurement is preferably made within approximately 300 usec of the flash start point and more preferably within approximately 200 usec of the flash start point. The level of transient fluorescence is compared with the steady state level of fluorescence. The difference between the two levels is a measure of the variable fluorescence and the functionality of the PS II system of the plant. A control plant may be used as a standard. The method preferably comprises subjecting the sample plant to additional flashes of light subsequent to the flash of light referred to above (that is, the flash of light referred to above preferably comprises a series of flashes of light) to bring about a series of fluorescent transients, and comparing the level of each fluorescent transient with the steady state level. The differences can then be averaged.

The invention also comprises a fluorimeter device for measuring variable fluorescence using the method of the invention. The fluorimeter can be used to assess the functionality of, or photoinhibitory damage to, a plant. The fluorimeter comprises a steady lamp to provide constant-level light (excitation energy) to bring about continuous, steady state fluorescence of a non-dark adapted, non-electron transfer blocked plant; a flash lamp to provide a flash of light (excitation energy) to bring about transient fluorescence of the plant; fiber optics to convey light from the steady lamp and the flash lamp to the plant; a photosensor to detect steady state and transient fluorescence from the plant; fiber optics to convey fluorescence from the plant to the photosensor; and electronic means electronically connected to the photosensor to measure and compare the steady state fluorescence with the transient fluorescence where the transient fluorescence is measured within 500 usec of the flash start point, or preferably within 300 usec of the flash start point, or more preferably within 200 usec of the flash start point. The fluorimeter device preferably comprises portable means for providing power, e.g., a battery unit. In portable form, the fluorimeter device further comprises means for conveying the foregoing components as a single unit.

The advantages of the invention over the prior art are several. There is no need to dark adapt samples. This not only saves the time of dark adaptation, but also means any type of plant in any type of setting can be measured. There is also no need to block electron transport. In addition, measurements can be taken on a very short time scale. Because of this, a series of measurements can readily be made for a given plant, thereby resulting in greater precision of result.

Measurements of a large number of plants can be made in the field under ambient light conditions with the invention, particularly using the device of the invention in portable form. It is therefore practical to undertake full scale breeding programs which rely on screening for photosynthetic function.

The invention is also particularly adapted for lab measurements of plants at an early stage of development and plant tissue culture samples, including calli and single cell suspension cultures.

FIG. 1 represents a schematic diagram of the fluorimeter device of the invention.

The invention will be further described with reference to FIG. 1. Steady lamp 1 provides a steady, continuous source of low level excitation radiation and brings about a continuous, low level, steady state fluorescence emission from a sample, thereby providing a baseline for assessing variable fluorescence. The sample is shown in FIG. 1 as a leaf. The steady light source provides visible light of blue color, e.g., in the approximate spectral region of 380 to 550 nm. The intensity of the light provided is preferably in the approximate range of $5 \times 10^3 - 2 \times 10^5$ erg/cm$^2$ sec. The steady light source preferably has an adjustable intensity. This permits the adjustment of the intensity to match ambient light intensity, thereby allowing a rapid measurement without concern as to slow physiological adjustment of the plant to the light source. The steady light source can be any broad-range, visible light source covering the spectral range as stated. Halogen lamps are preferred, such as Sylvania type 1990 12 W halogen lamp.

Lamp intensity control 2 is connected to steady lamp 1 by wire 2a. (For wire 2a and other wires in FIG. 1, a single line is shown to represent one or more wires providing the stated connection.) The lamp intensity control provides that the steady lamp will put out the needed amount of light. Preferably, the lamp output is sensed with photodiode 3 (connected to the lamp intensity control by wire 3a) with blue filter 4. Changes in lamp characteristics will not alter the final light output. The control circuitry of the lamp intensity control provides power to the steady lamp so that the electrical signal from the photodiode matches a reference signal set on front panel 18 and conveyed by wire 18a. The control of power to the steady lamp may be accomplished with a power transistor that governs current flow to the lamp either in a constant current mode or, alternatively, in a switching mode.

Flash lamp 6 generates an intense actinic flash (superimposed on the steady light) which results in the fluorescence transient (the flash transient). The flash lamp (alternatively, the strobe light or stroboscope) provides visible light, preferably of blue color. A laser source can be used. A preferred flash lamp is EG&G 9B1.5. The flash energy should be in the range of 50 to 5000 ergs/cm$^2$ per flash, with approximately 200 to 1000 ergs/cm$^2$ per flash preferred. In comparison with the light from the steady lamp, the maximum intensity of the flash in units of ergs/cm$^2$ sec (as opposed to ergs/cm$^2$ per flash) should be about 10 to about 10$^7$, and preferably about 10$^3$ to about 10$^6$, times the energy of the light from the steady lamp for the corresponding time period. The width of the flash curve (intensity, vertical axis versus time, horizontal axis) is normally within the range of about 1 usec to about 50 usec ("width" meaning the time of 50% maximum intensity on the ascending part of the curve to the time of 50% maximum intensity on the descending part of the curve). The width can be somewhat lower if the flash energy level is maintained. A preferred width is from about 3 usec to about 10 usec. Each measurement of flash fluorescence is preferably based on the averaging of measurements for a series of flashes. Where a series of flashes is used, the frequency of the generated flash is from about 1 flash/sec to about 100 flashes/sec. A preferred frequency is from about 5 flashes/sec to about 20 flashes/sec with about 10 flashes/sec being particularly preferred.

Flash lamp driver 5 is connected to flash lamp 6 by wire 5a. The flash lamp driver is a unit which provides high voltage power, stored in a capacitor, to the flash lamp. The flash lamp driver provides a trigger pulse to initiate lamp discharge, also carried on wire 5a. The flash lamp and flash lamp driver can be a single unit, e.g., Gen Rad 1539-A Stroboscope. A preferred flash lamp driver is EG&G model PS 350. Flash lamp driver 5 is connected by wire 15a to flash lamp timer 15, a unit which controls the frequency of the flash and synchronizes fluorescence measurement with the flash.

Light from flash lamp 6 initially passes through condensor lens 7, which gathers the light and focuses it at the end of fiber optics branch 10a. Light from steady state lamp 1 passes through condensor lens 8, which performs a similar function. Each of condensor lenses 7 and 8 can be one or more lenses. The lenses are standard condensor lenses. A preferred arrangement is a pair of 22 mm diameter, 18 mm focal length aspheric glass lens such as Melles-Griot model 01 LA6 005 lens. After passing through the condensor lenses, but before entering the fiber optics, the light passes through filter 9 to remove red light of wavelength of greater than 650 nm, so as to avoid interference with the measurement of fluorescence. That is, red is the color of light emitted by the fluorescing plant, and if the fluorescence is to be accurately measured it is preferable to filter out red light from the steady light source. A blue filter is preferred, e.g., Corning filter 4-96 which passes light of approximately 380 nm to 550 nm. Notch filters may be used. The lamps, lens, and filter are preferably positioned within carrier 11, to which fiber optics are attached via the end of fiber optics branch 10a. Carrier 11 is a unit to position and hold the described components.

Light is conveyed from the steady and flashing light sources to the sample via means for conveying incident light, and fluorescence is conveyed from the sample to a photosensor via means for conveying fluorescent (emitted) light. The means for conveying incident light and means for conveying fluorescent light (collectively, the probe) are preferably fiber optics means, as explained below. The incident and fluorescent light can be conveyed via the air, but this is not a preferred mode. With reference to FIG. 1, incident light is conveyed from the steady lamp and the flash lamp to the plant by fiber optics positioned with relation to the steady lamp and the flash lamp (i.e., positioned and aligned so as to be able to so convey the light). In FIG. 1, the fiber optics positioned with relation to the steady lamp and the flash lamp are fiber optics branch 10a and fiber optics trunk 10 (the fiber optics probe). Fluorescent light (emitted light) is conveyed from the plant to photosensor 12 by fiber optics positioned with relation to the photosensor (i.e., positioned and aligned so as to be able to so convey the light). In FIG. 1, the fiber optics positioned with relation to the photosensor are fiber optics trunk 10 and fiber optics branch 10b. The fiber optics can be any fiber optics that transmit visible light. Low-loss glass fiber is preferred. A preferred type is Dolan-Jenner model E 836 fiber optics. If the invention is used without fiber optics, a probe can be employed which holds the two light sources and the sensing mechanism in proper alignment. This is not preferred in that such a probe would be bulky, delicate and susceptible to electronic noise pick-up.

A random mixture of fibers from the two branches 10a and 10b is preferred for fiber optics trunk 10. If this is not the case, it may be helpful to use a collimator lens at the end of fiber optics trunk 10 nearest the plant to focus the light on the plant. Also, if remote sensing is desired, i.e., if the fiber optics probe is to be held a distance (e.g., 1 cm) from the plant rather than touching it, a lens assembly at the plant end of fiber optics trunk 10 can be used to focus the image of the fiber optics on the plant.

Photosensor 12 (a photodetector) receives fluorescence (steady state and transient) from the plant (via fiber optics branch 10b), converts this into an electrical output signal proportional to the received fluorescence level, and provides this output signal to measurement electronics 14. The photosensor preferably is a photodiode-transistor unit ("phototransistor"), for instance model ECG 3037 phototransistor. Alternatively, a photomultiplier can be used. Red filter 13 is preferably used in conjunction with the photodetector, for instance, Kodak Wratten filter 70 "Deep Red". The purpose of the filter 13 is to filter out light other than that of the fluorescence emission, in particular, to filter out the blue light used to illuminate the sample.

The transient fluorescence immediately after a flash is compared with steady state fluorescence by means of measurement electronics 14 (electronic means to measure and compare the steady state and transient fluorescent levels), which is electrically connected to photosensor 12. The measurement electronics receives an output signal from the photosensor. The measurement electronics measure and compare the level of steady state fluorescence and the level of transient fluorescence, where the level of transient fluorescence is measured preferably within approximately 500 usec of the flash start point, more preferably within approximately 300 usec of the flash start point, and most preferably within approximately 200 usec of the flash start point. The measurement electronics preferably can measure and compare a series of fluorescent transients resulting from a series of flashes. The measurement electronics comprises a current sensing amplifier, sample and hold current nulling circuitry (first sample and hold circuitry), and sample and hold transient measurement circuitry (second sample and hold circuitry).

The photosensor conducts an amount of current dependent on the incident light intensity. This current source is used to control the base current of a transistor. Auxiliary circuitry provides that this transistor is correctly biased relatively independent of temperature or supply voltage, and that its response time is fast enough to follow accurately the fluorescence transient. The collector of this transistor provides a current signal to the current sensing amplifier.

The current sensing amplifier converts current at its input (from the photosensor) to an output voltage. This amplifier should have high input impedance, good noise characteristics, and a unity gain bandwidth of at least $10^6$ Hz. An example of an acceptable amplifier is model LF 353 (Fairchild Electronics), which is a dual amplifier. The second amplifier can be used for additional voltage amplification.

Current nulling is provided by sample and hold current nulling circuitry (first sample and hold circuitry). For a period of time preceding the flash, from 100 milliseconds (msec) to 1 msec before the flash, and most preferably for 10 msec before the flash, the sample and hold current nulling circuitry is in the "sample" mode. The hold capacitor settles within this time. The output of the current sensing amplifier is highly amplified and sampled. The hold amplifier provides a current signal to the input of the current sensing amplifier sufficient to result in a null signal at the output of the current sensing amplifier. The current signal from the hold amplifier is proportional to the steady state fluorescence of the sample. The sample and hold current nulling circuitry goes into "hold" mode when the trigger signal is sent to the flash lamp, so a current signal sufficient to null out steady state fluorescence is sent to the current sensing amplifier and the signal appearing at the output of the amplifier is composed only of deviations from the steady state. The hold capacitor should show negligible droop (discharge of the hold capacitor resulting in a change in output of the sample and hold circuit) between flashes.

The sample and hold current nulling circuitry, as well as the sample and hold transient measurement circuitry described below (second sample and hold circuitry), can be a commercial device such as National Semiconductor monolithic sample and hold model LF 198. Alternatively, sample and hold circuitry can be assembled, as will be understood by one skilled in the art, from the following standard components: four diodes such as type IN914 arranged to act as a signal gate; a hold capacitor; and an operational amplifier buffer with FET (Field Effect Transistor) input such as Texas Instruments operational amplifier TL062.

The signal from the current sensing amplifier goes to a second sample and hold circuitry (sample and hold transient measurement circuitry). This circuit samples the signal from the current sensing amplifier at a time shortly after the flash. The afterglow from a flash lamp takes some time to completely decay, usually between 100 and 200 msec, depending on details of the lamp and associated circuitry. This afterglow will give the appearance of a fluorescence transient even though none exists. Lamp glow can be eliminated by use of a laser light source or by chopping the flash lamp light with an electronic shutter or tuning fork.

The second sample and hold circuitry samples for a period of about 20 usec. The hold capacitor need not settle fully within the sample period. If it does not, this will result in averaging of the signal for a number of flash periods, and a response time that is longer than the minimum attainable. Preferably, the response time is about 5 to 20 sec to 90% of final signal.

The timer unit 15 generates a series of electrical pulses. These are: (1) a pulse sent to the sample and hold current nulling circuitry of measurement electronics 14 via wire 15b; (2) a pulse sent to the flash lamp driver 5 via wire 15a resulting in triggering of the flash lamp if the flash lamp is enabled by a logic signal from front panel 18 and carried by wire 18b; and, (3) a pulse sent to the sample and hold transient measurement circuitry of measurement electronics 14 via wire 15b resulting in signal sampling. These pulses can be generated by circuitry that is readily designable by one skilled in the art based on I.C. timers such as Texas Instruments model NE555. The duration of the first pulse is such that the current nulling circuitry has time to settle. The hold capacitor of the sample and hold should show negligible droop in the interval between flashes. Preferably, the current nulling pulse duration is approximately 1/10 of the period between flashes, or 10 msec for a flash frequency of 10/sec. The second pulse is sent immediately after the first pulse, and is of sufficient duration to result in flash lamp triggering, no greater than about 1 microsecond. The third pulse is sent at a time after the second pulse such that signal measurement occurs after the flash from the flash lamp is completely decayed. Measurement starts most preferably immediately after the flash. The light pulse from the flash lamp must decay so that it is a small fraction of the intensity of the steady lamp, so that flash glow does not interfere with the fluorescence signal induced by the steady lamp. Measurement should occur when the light pulse from the flash lamp is less than 10% of the steady lamp intensity, and preferably less than 1% of the steady lamp intensity. The duration of the third pulse is long enough to permit signal sampling, but short compared to the rate of change of the fluorescence transient signal. Signal sampling occurs preferably over a period of 1 to 50 usec, and more preferably over a period of 10 to 20 usec.

Panel meter 19 can be used to display data. The output signal is carried from measurement electronics 14 to panel meter 19 by wire 19a. A preferred panel is an LCD meter for good sunlight visibility. Analog meters are acceptable as well. The output signal can also be connected to a chart recorder or a data logger where time courses or permanent records are required. Both transient size and steady state fluorescence can be displayed. The transient size is the difference between fluorescence after the flash and the steady state fluorescence. Zero adjustment for both steady state fluorescence and transient size is provided on front panel 18 and carried by wires 18e and 18f. The signal resolution of the panel meter is preferably 1% or better.

A fast A/D converter and digital memory to convert a decay transient to digital form may be used for the measurement and analysis of fluorescence decay kinetics. A digital interface may be used to convert analog signals to digital form for computer interface.

The means for providing power to the various components described above can be a conventional electrical outlet or a conventional battery (this can actually be one or more batteries). For a portable device, the source of power is preferably a battery together with transformer 20. Battery 16 is used to provide power via an on/off switch on the front panel 18 and wire 18g to the power supply board 17. The power supply board 17 provides for A/C operation and battery charging with external transformer 20. Transformer 20 provides A/C power to power supply board 17 via wire 20a. Battery 16 is used to provide power for the steady lamp via the lamp intensity control 2 by way of wire 16a, the on/off switch on front panel 18, and wire 18d, and to flash lamp 6 via flash lamp driver 5 by way of wire 16a, the on/off switch on front panel 18, and wire 18c. Batteries for field operation are preferably rechargeable, and preferably operable in any position. NiCad, gel or suspended electrolyte type lead acid batteries can be used. An adequate battery for the purpose is Yuasa NP 6-12. Voltage regulation is accomplished by voltage regulators on power supply board 17, and distributed to lamp intensity control 2, timer 15, measurement electronics 14, panel meter 19 and front panel 18 via wires 17a, 17b, 17c,17d and 18g.

Where the device is a portable unit, the unit also comprises a suitable means for carrying the previously described components. The various parts are preferably mounted on a chassis enclosed in a box, e.g., of approximate dimensions 15"×10"×4.5" with a total assembled weight of about 15 pounds. The box is preferably provided with a carrying strap.

The fluorimeter device of the invention is used to make measurements of plants which are non-dark adapted (i.e., ambient light conditions) and which have not been treated with transport blocking agents (i.e., free electron flow plants). As used herein, the terms plant or plant sample shall be taken to mean any green plant, either in the form of a whole plant; a plant part (e.g., leaf or stem); a plant preparation (e.g., thylakoid or other chloroplast preparation); a tissue culture sample (e.g., explant or callus); a cell suspension culture (single or clumped); or a photosynthetic single cell organism, eukaryotic or prokaryotic.

The invention is based on the finding that variable fluorescence can be measured using fluorescent transients as disclosed herein. The method shall be referred to herein as the flash variable fluorescence method. Variable fluorescence measured in accordance with the invention shall be referred to herein as flash fluorescence increase.

In accordance with the method of the invention, a fluorescent transient is measured at a point in time within several msec (e.g., 3-4 msec) of the flash start point, with the measurement preferably made within about 500 usec of the flash start point, more preferably within about 300 usec of the flash start point and most preferably within about 200 usec of the flash start point. The flash start point is the point in time when the flash begins to emit light. This point corresponds substantially to the point in time of electronic triggering of the flash lamp (the triggering occurs on the scale of nanoseconds, or less). The measurement of the fluorescent transient is preferably made at a point in time subsequent to the flash end point. The flash end point is defined for present purposes as the point in time at which the glow from the flash drops to a level of approximately equal to or less than 10% of the level of light from the steady lamp (described further below). The flash end point can be determined by running the system without sample and determining the time for the glow of the flash to decay to that level. For laser flash lamps the flash end point may be on the order of several usec subsequent to the flash start point; for other lamps the flash end point may be on the order of 10-300 usec subsequent to the flash start point. Measurement of the transient earlier than the flash end point can lead to problems of interference from the flash glow. A preferred method of operation is to measure the transient at a point in time substantially corresponding to the flash end point.

Steady state fluorescence is also measured before the flash to provide the baseline level to be subtracted from the transient level to yield the variable fluorescence increase value. If a series of flashes is used, as is preferred, the individual flashes are separated by a sufficient period of time (flash separation) one from the next, e.g., from 10 msec to 1 sec, to allow the transient to return substantially to the baseline level in between flashes. For best signal resolution the flash separation should be closer to the lower end of the range. Each transient is compared with the baseline and a number of signals are averaged.

Variable fluorescence, determined in accordance with the method of the invention, correlates with variable fluorescence measured by other methods. For instance, in comparison with the electron-blocked variable fluorescence method, the level of the fluorescent transient is directly related to $F_{max}$ (the relationship coefficient depends on how long after the flash end point the transient is measured and the efficiency of light measurement), and the level of the steady state fluorescence is directly related to $F_o$.

The transient fluorescence increase for a given plant sample is preferably compared with that of an appropriate control in order to assess the functionality of the PS II system of the plant sample. The control can be a similar plant of known photosynthetic functionality, e.g., a stress-resistant or stress-sensitive variety of the same plant. Where the susceptibility of a plant to a given stress is to be determined, the control for the plant subjected to stress may be the plant prior to application of the stress.

While the invention is not limited by underlying theory, an explanation of the theory is that upon illumination of a plant sample with a bright flash of light, there is a resultant rapid (less than 1 usec) transfer of an electron within PS II from $P_{680}$ to $Q_A$. With $Q_A$ in its reduced state, PS II is fluorescent. Under normal in vivo conditions, this electron is passed to subsequent electron carriers with half times for transfer on the order of 250 to 2000 usec. For example, in rice there is a mixture of decay times with about 50% 300 usec half time and 50% 1300 usec half time. $Q_A$ is thus oxidized, a state in which fluorescence is quenched. By application of a flash in accordance with the invention, there is an immediate fluorescence transient (corresponding to reduced $Q_A$). The kinetics of the fluorescence decay follow the redox state of $Q_A$. This sequence can be repeated for a series of flashes. The peak of the fluorescence transient is somewhat less than the $F_{max}$ measured under electron transport blocking conditions, because of various in vivo controls on PS II activity. If electron transport is light limited and the photosynthetic apparatus is fully functional and the flash intensity is great enough to bring about electron transport in close to all of the reaction centers, the peak fluorescence will be equal to $F_{max}$. The baseline fluorescence level (i.e., after full decay) is somewhat greater than $F_o$ measured under electron transport blocking conditions, because under normal in vivo conditions $Q_A$ is not fully oxidized (it is on the order of 90% oxidized).

The invention can be used in the field, in the greenhouse, in the growth chamber or in any other setting in which a plant is growing, to measure the variable fluorescence of plants, either in vivo or removed, under ambient light conditions. Such measurements, particularly for field plants, are best taken using the device of the invention in its portable form. With such measurements the plant is analyzed under natural growth conditions and the analysis is a realistic estimate of the plant's ability to perform under those conditions. The measurement is taken by holding (preferably touching) the probe (preferably, a fiber optics probe as described above) to the plant and obtaining a readout of the variable fluorescence value. For each sample measurement it is preferred that the series of flashes comprises at least several flashes and preferably about 10 to about 200 flashes (with the specific number to be selected turning on considerations of response time and measurement accuracy). With the invention, using a series of flashes and averaging, as preferred, the measurement can be made in a short period of time, e.g., 15 seconds (corresponding, for instance, to about 150 flashes and thus about 150 readings). The $F_v$ value is compared to that of an appropriate control in order to assess the extent to which electron transport through PS II is occurring (that is, to assess the extent of any photosynthetic stress damage to the plant).

The susceptibility of a plant to a given stress is determined as follows. The flash variable fluorescence of the plant is determined, in accordance with the method of the invention as described above, prior to application of the stress and again subsequent to application of the stress. That is, the unstressed plant is illuminated with light from a steady lamp to bring about a steady state level of fluorescence, which is measured. The unstressed plant is then exposed to a flash of light (first flash of light) to bring about transient fluorescence which is measured preferably within approximately 500 usec, more preferably within approximately 300 usec, and most preferably within approximately 200 usec of the exposure of the plant to the flash of light. The variable fluorescence of the unstressed plant is determined by comparing the level of transient fluorescence of the unstressed plant with the steady state level of fluorescence of the unstressed plant. This value is preferably used as the comparison standard (reference value) with respect to the variable fluorescence of the stressed plant, which is determined as follows. The unstressed plant is subjected to a photoinhibitory stress to yield a stressed plant. The stressed plant is illuminated with light from a steady lamp to bring about a steady state level of fluorescence, which is measured. The stressed plant is then exposed to a flash of light (second flash of light) to bring about transient fluorescence which is measured preferably within approximately 500 usec, more preferably within approximately 300 usec, and most preferably within approximately 200 usec of the exposure of the plant to the flash of light. The variable fluorescence of the stressed plant (sample value) is determined by comparing the level of transient fluorescence of the stressed plant with the steady state level of the stressed plant. Comparison of the variable fluorescence of the unstressed plant with the variable fluorescence of the stressed plant provides a measure of the susceptibility of the plant to the photoinhibitory stress. If the reference value and the sample value are substantially the same, this is evidence of the absence of stress damage and the non-susceptibility of the plant to stress damage. To the extent the sample value is lower than the reference value, this is evidence of stress damage in the plant and susceptibility of the plant to damage.

In the method for determining the susceptibility of a plant to a photoinhibitory stress, the preferred features described above for the method of determining variable fluorescence are again preferred. Thus, in determining variable fluorescence values for both the unstressed and stressed plants, the level of transient fluorescence in each instance (unstressed plant and stressed plant) is preferably measured at a point in time subsequent to the corresponding flash end point; the flash of light in each instance (first flash of light and second flash of light) is preferably a series of flashes of light to bring about a series of fluorescent transients (first series of fluorescent transients and second series of fluorescent transients) and the comparing of transient and steady state fluorescence levels in each instance comprises comparing and averaging each fluorescent transient level in the series of transients with the corresponding steady state level; and, where a series of flashes is used, in each instance the series preferably comprises between about 10 and about 200 flashes.

The invention can be readily used with plants at an early stage of development, so that a shorter period of growth is required in order to get significant measurements (compared to yield measurements). Measurements can be taken on seedlings with as little as 10 mm$^2$ leaf area. This is of importance where the invention is used in breeding programs, as described below.

The invention can also be used on tissue culture samples. This can be done by positioning the probe on or near the sample or, preferably, touching the probe to a container holding the sample, e.g., the cover of a Petri dish containing calli. Such measurements are taken much more readily with the method of the invention than with alternative methods, e.g., use of the Brancker Plant Productivity Meter, for several reasons. First, there is no need to dark adapt. Second, callus has a lower density of photosynthetic apparatus per cell than cells of whole plants, and fluorescent signals are accordingly considerably weaker. Because the method of the invention employs a brighter light source, it is easier to obtain fluorescence signals. Third, because of the brightness of the light source, measurements can be taken at short distances, e.g., 1 cm, from the tissue culture sample. Thus, one can measure samples, e.g., calli, through the lid of a Petri dish without need to open the dish or touch the samples, thereby avoiding contamination problems. Also, because of the speed with which measurements can be taken, hundreds or thousands of samples can be measured on a workable basis.

The invention can be used as well on single cell suspension cultures. For qualitative assessment of photosynthetic competence, the probe can be touched to the wall of a transparent growth vessel in the vicinity of the growing cells. For physiological experiments, such as herbicide tolerance tests, an aliquot can be withdrawn and the probe immersed in the suspension.

The invention provides a means to select improved plant varieties. Specifically, the invention provides a means to assess the tolerance of a plant to a photoinhibitory stress factor. The procedure to be followed is, first, to establish the average range of variation for a population of plants (so as to know what a significant deviation is). A group of test plants is then subjected to an episode of stress, and subsequently returned to normal conditions. At this point the $F_v$ value for each plant is again measured. Comparison of the $F_v$ value for a given plant before and after the stress episode provides a measure of the ability of the plant to function normally during the stress and a measure of tolerance of the plant to damage from the stress. A decline in the $F_v$ value is indicative of the occurrence of damage during the stress period. A stress tolerance breeding program can thus be based on making measurements of a large number of plants and selecting individuals showing significantly improved tolerance to stress.

The invention also has utility in other contexts. First, the invention can be used to determine least-cost greenhouse heating schedules. By measuring $F_v$ for a series of night temperature drops, one can determine the point at which chill stress effects appear. Greenhouse night temperatures can then be kept above that point. Second, in analogous fashion, least-cost irrigation schedules can be determined by measuring $F_v$ for progressively decreased irrigation levels and finding the point at which stress effects appear due to lack of water. Third, plants can be screened for tolerance to photoinhibitory herbicides by making $F_v$ measurements of the plant before and after treatment with herbicide. This approach is particularly suited for plants regenerated from tissue culture and can be used, as explained above, in measurements on tissue culture samples. Fourth, the invention provides a means to screen chemical compounds for photoinhibitory herbicide activity, again by measuring $F_v$ values of sample plants before and chemical treatment. In addition, the invention provides a way to assess photosynthetic well being of a plant in various stages of tissue culture development.

The invention further provides a means of obtaining information about the physiology and biophysics of photosynthesis. It provides a means for the assessment of PS II electron transport independent of gas exchange, which can have multiple contributions technically difficult to separate. It also provides a means for continuous monitoring of electron transport rates during experimental conditions such as temperature shifts or $CO_2$ or oxygen deprivation that would be difficult to do with gas exchange techniques, since the latter depend on constant temperature and gaseous environment. This capability is valuable in the characterization of stress effects on photosynthesis.

In conjunction with a storage oscilloscope or other fast data acquisition equipment, the invention can be used to generate fluorescence decay transients from material photosynthesizing under in vivo conditions. This permits study of the biophysics of electron transport in photosystem II under in vivo conditions.

EXAMPLE 1: LOSS OF FLASH VARIABLE FLUORESCENCE AFTER STRESS

A. Instrumentation

Flash variable fluorescence ($F_v$ measured in accordance with the invention) was measured using steady illumination with saturating flash superimposed, together with electronics to allow the measurement of the magnitude of the flash-induced fluorescence transient. The saturating flash was provided by General Radio Stroboslave model 1539-A flashlamp, the steady illumination by a type DZA 30W G.E. incandescent lamp, and condensor lenses to focus a 1x image of the gas discharge zone and filament of the lamps on one leg of a bifurcated fiber optic. One leg of the bifurcated fiber optics (Dolan-Jenner model EE436) was used to bring the illuminating light to the sample, and the other half was used to bring the resulting fluorescence to the photodetector (ECG 3037). The two bundles of the fiber optic were split into two distinct halves. Collimating lenses were used at the sample end of the fiber optics to illuminate and measure a given area of a leaf optic.

The electronics consisted of a timer, lamp intensity control (voltage regulator), and measurement electronics. The measurement electronics consisted of a current sensing amplifier (Fairchild Electronics model LF 353), sample and hold current nulling circuitry, and sample and hold transient measurement circuitry. Each of the sample and hold circuits was assembled from four diodes (type 1N914) arranged to act as a signal gate; a hold capacitor; and Texas Instruments operational amplifier TL062. Power was provided by rechargeable batteries. The timer, constructed based on type 555 I.C. timers, provided a signal before the flash to trigger the sample and hold current nulling circuit. When triggered, this circuit adjusted the amplifier output to zero by applying an offset current to the phototransistor collector. This current was maintained in hold mode. The timer then provided a signal to the Stroboslave, causing the xenon lamp to flash. The timer then provided a signal to the sample and hold transient measurement circuit. When triggered, it sampled the fluorescence signal at a time early in the decay of the flash induced fluorescence, but late in the decay of the flash lamp glow. This point was determined by observing the fluorescence decay both with and without a steady light source, using a Nicolet Model 4094 storage oscilloscope with signal averaging. Without a steady light source, signal decay was due essentially to the decay of the glow from the flash lamp. With the flash lamp at maximum intensity, 200 microseconds was used as the measurement time. The signal collected at this time was accumulated in the hold capacitor, with the output of the hold amplifier being the average of several measurement cycles. Averaging 20 to 200 measurements gave acceptable accuracy and response time. The offset current provided to the collector of the phototransistor was proportional to the steady state fluorescence, after subtraction of dark current, allowing both parameters to be measured simultaneously.

B. Experiment

Leaves of a chilling sensitive cultivar of rice IR8 from the U.S.D.A. Small Grains Collection were detached from the plant and subjected to various treatments. Material was taken from a ten week old plant. Samples were subjected to one of the following treatments: (1) $2 \times 10^5$ ergs/cm$^2$ sec white light and 25° C.; (2) 5° C. at the same light intensity; (3) 5° C. in the dark; (4) $10^{-5}$ M diuron. Leaf segments were floated on water in petri dishes, except for the diuron treated leaf segment, which was placed in a test tube with its basal end in the diuron solution, to permit transpirational uptake of the inhibitor. Temperature was maintained by floating the petri dishes in a water bath at the appropriate temperature. A Kodak 4000 slide projector was used as a light source. Conditions were maintained for 2 hours, after which time measurements were made within 15 minutes. Steady lamp intensity was adjusted to approximately 15000 ergs/cm$^2$ sec. The flash lamp provided a flash energy of approximately 100 ergs/cm$^2$, at a frequency of 15 Hz (15 flashes per second). The size of the fluorescence transient (the output of the sample and hold) was measured in millivolts with a digital multimeter.

Plants to be measured were held under room lights, and measurements were made in room light conditions. Measurements were made by touching the end of the probe to the surface of the leaf segment, and adjusting the output reading to zero with only the flash on. The steady lamp was turned on and the fluorescence transient size read on the millivolt meter as soon as it had settled to a steady reading, within 5 seconds.

C. Results

The results are shown on Table I.

TABLE I

| Plant | $F_v$ (millivolts) |
|---|---|
| Control | 67 |

TABLE I-continued

| Plant | $F_v$ (millivolts) |
| --- | --- |
| Chilled in dark | 70 |
| Chilled in light | 14 |
| Diuron treated | 0 |

The results show inhibition of the fluorescence signal from the material subjected to chilling in the light compared to the control treatments of illumination at ordinary temperature and chilling in the absence of light. With respect to the diuron treated material, the results demonstrate the absence of a fluorescence transient.

EXAMPLE 2: FLASH VARIABLE FLUORESCENCE IN A PSII MUTANT

A. Instrumentation

Instrumentation for this experiment was the same as for Experiment 1.

B. Experiment

Measurements were made as described in Example 1, except that leaves were not detached from plants and measurements were of plants in the greenhouse under ambient light. Measurements were made on fully expanded leaves of a photosystem II mutant and a control normal plant. The mutant used was a variegated *Nicotianum tobaccum*. The mutation was manifested as light green and yellow green regions of the otherwise green leaf surface. The mutation is known to affect PS II activity. The control plant was a normal *Nicotianum tobaccum*. Both plants were regenerated from tissue culture, transplanted to pots and grown in the greenhouse to a height of approximately 12 inches.

C. Results

The results are shown in Table II.

TABLE II

| Plant | $F_v$ (millivolts) |
| --- | --- |
| Control (triplicate measure) | 94, 87, 100 |
| Sample | |
| Green | 102 |
| Light green | 55 |
| Yellow green | 10 |

The results are consistent with a lack of full functionality of the light green and yellow green regions of the mutant plant. The results demonstrate that the device can be used to detect photosynthetic mutations that result in low rates of electron transport through photosystem II.

EXAMPLE 3: Comparison of the flash variable fluorescence method with the electron blocked variable fluorescence method and the Kautsky effect variable fluorescence method.

A. Instrumentation (1) Flash Variable Fluorescence

Instrumentation for this experiment corresponded to that of Examples 1 and 2, but utilized fiber optics with fibers from the two legs randomly mixed in the common bundle (Dolan-Jenner model E836). Data were recorded with a Bascom-Turner digital chart recorder model 3120T.

(2) Electron Blocked Variable Fluorescence

Measurements were made with a Perkin-Elmer model 650-40 fluorimeter modified for kinetic measurements and provided with a Uniblitz model 225L shutter to control illumination. Data was collected with a Nicolet 4094 digital oscilloscope.

(3) Kautskv Effect Variable Fluorescence

The Branker Plant Productivity Fluorimeter, Model SF 10 was used, together with the Nicolet oscilloscope.

B. Plant Material

Four plants were tested: cold grown barley, greenhouse grown barley, and rice cultivars M201 and IR8. The barley (cv. Himalaya) was grown in a Percival growth chamber at 10° C. for four weeks prior to use for cold grown barley or in a greenhouse for two weeks. Barley is chilling tolerant compared to rice, and growth at 10° C. results in some increase in chilling tolerance. Rice seed was obtained from the U.S.D.A. Small Grains Collection (IR8) or from the California Rice Growers Association (M201). Rice was grown in the greenhouse and used between 8 and 12 weeks after germination.

Portions of undetached leaves of each plant were subjected to chilling stress as follows. The samples were placed on a 5° C. temperature controlled plated and subjected to illumination at $4 \times 10^5$ ergs/cm$^2$ sec of white light for two hours. The samples were then left for two hours at 25° C. in room light, permitting recovery of short term adaptation of PS II to high light (so that short term effects were not measured). At this time samples were taken from the stressed and unstressed portions of the leaves and measurements taken.

C. Experiment (1) Flash Variable Fluorescence

Measurements were made as in Example 2.

(2) Electron Blocked Variable Fluorescence

Electron transport was blocked by incubation for two hours in a solution of $10^{-5}$ M diuron and 0.01% Tween 80. Measurements were made with the illumination controlled by a shutter and the transient recorded on the oscilloscope. The height of the fluorescence transient, which reached a steady state within 200 msec, less the fluorescence immediately after shutter opening, was calculated. Samples were dark adapted for at least 10 minutes before measurement.

(3) Kautsky Effect Variable Fluorescence

Measurements were made in accordance with directions distributed by the manufacturer of the fluorimeter. Transients were recorded by oscilloscope. The height of the fluorescence peak less the fluorescence at the start of illumination was calculated. Leaf segments were dark adapted for at least 20 minutes before measurements were made.

D. Results

The results are shown in Table III. Measurements are expressed as a percentage of the values obtained for the corresponding control (unstressed leaf surface from the same plant).

TABLE III

| Plant | Flash Variable Fluorescence | Electron Blocked Variable Fluorescence | Kautsky Effect Variable Fluorescence |
|---|---|---|---|
| Cold Grown Barley | 93, 71, 85, 78 | 81, 80 | 71, 84, 83 |
| Greenhouse Grown Barley | 70, 65, 52, 58, 47, 53, 69 | 58, 67, 83 | 54, 55 |
| Rice M201 | 30, 28, 39, 37 | 33, 35, 57 | 32, 20, 37 |
| Rice IR8 | 12, 17 | 28 | 21, 25 |

The results show that data obtained with the method of the invention are consistent with readings obtained with prior methods. In addition, the results illustrate the use of the device for the determination of stress induced loss of photosynthetic capacity. This shows that the device can be used to screen for stress tolerance.

EXAMPLE 4: COMPARISON OF FLASH VARIABLE FLUORESCENCE VALUES WITH OXYGEN EVOLUTION RATES

A. Instrumentation (1) Flash Variable Fluorescence Method

Instrumentation is the same as for Example 3.

(2) Oxygen Evolution

Oxygen levels were measured using a Clark electrode (Yellow Springs Instrument Co. model 53), and a temperature controlled chamber designed to be illuminated with the fiber optics probe from the fluorescence transient measurement device. Oxygen levels were recorded on a Bascom-Turner digital chart recorder, and rates calculated.

B. Experiment

Using a leaf disk from a greenhouse grown barley plant, simultaneous measurements were made of oxygen evolution and size of fluorescence transient over a range of light intensities. All measurements were made at 25° C.

C. Results

The results are shown in Table IV. $F_v$ and oxygen evolution are expressed as a percentage of the median value attained at the highest light intensity. $F_v$ was not constant throughout the time required for oxygen evolution rate determinations, so a range is given. The maximum oxygen evolution rate for this system was approximately 150 umol/min cm$^2$.

TABLE IV

| Light Intensity (ergs/cm$^2$ sec) | $F_v$ | Net Photosynthetic Oxygen Evolution |
|---|---|---|
| 0 | 0 | 0 |
| 12,000 | 24–27 | 24 |
| 17,500 | 46–47 | 51 |
| 37,500 | 66–69 | 71 |
| 52,500 | 86–98 | 86 |
| 73,000 | 86–113 | 100 |

The results show a correspondence between photosynthetic electron transport rate as measured by oxygen evolution and as measured by fluorescence transient signal size under conditions of moderate light and temperature.

What is claimed is:

1. A method for measuring variable fluorescence of a plant, which comprises:
    (a) illuminating a plant with light from a steady lamp to bring about a steady state level of fluorescence;
    (b) measuring the steady state level of fluorescence;
    (c) exposing the illuminated plant to a flash of light to bring about transient fluorescence of the plant;
    (d) measuring the level of transient fluorescence within approximately 500 usec of the exposure of the plant to the flash of light; and
    (e) comparing the level of transient fluorescence with the steady state level of fluorescence to determine the variable fluorescence of the plant.

2. The method of claim 1 wherein the level of transient fluorescence is measured within approximately 300 usec of the exposure of the plant to the flash of light.

3. The method of claim 1 wherein the level of transient fluorescence is measured within approximately 200 usec of the exposure of the plant to the flash of light.

4. The method of claim 1 wherein the level of transient fluorescence is measured at a point in time subsequent to the flash end point.

5. The method of claim 1 wherein the flash of light comprises a series of flashes of light to bring about a series of fluorescent transients and wherein comparing the level of transient fluorescence with the steady state level of fluorescence comprises comparing each fluorescent transient in the series of fluorescent transients with the steady state level of fluorescence and averaging the differences.

6. The method of claim 5 wherein the series of flashes comprises between about 10 and about 200 flashes.

7. The method of claim 1 wherein said determination of the variable fluorescence further comprises comparison with the variable fluorescence of a control plant.

8. The method of claim 1 wherein the plant is a plant which has been subjected to photoinhibitory stress.

9. The method of claim 8 wherein the photoinhibitory stress is chilling stress.

10. A method for determining the susceptibility of a plant to a photoinhibitory stress, which comprises:
    (a) illuminating an unstressed plant with light from a steady lamp to bring about a steady state level of fluorescence of the unstressed plant;
    (b) measuring the steady state level of fluorescence of the unstressed plant;
    (c) exposing the illuminated unstressed plant to a first flash of light to bring about transient fluorescence of the unstressed plant;
    (d) measuring the level of transient fluorescence of the unstressed plant within approximately 500 usec of the exposure of the unstressed plant to the flash of light;
    (e) comparing the level of transient fluorescence of the unstressed plant with the steady state level of fluorescence of the unstressed plant to determine the variable fluorescence of the unstressed plant;
    (f) subjecting the unstressed plant to a photoinhibitory stress to yield a stressed plant;
    (g) illuminating the stressed plant with light from a steady lamp to bring about a steady state level of fluorescence of the stressed plant;
    (h) measuring the steady state level of fluorescence of the stressed plant;
    (i) exposing the illuminated stressed plant to a second flash of light to bring about transient fluorescence of the stressed plant;

(j) measuring the level of transient fluorescence of the stressed plant within approximately 500 usec of the exposure of the stressed plant to the flash of light;

(k) comparing the level of transient fluorescence of the stressed plant with the steady state level of fluorescence of the stressed plant to determine the variable fluorescence of the stressed plant; and (l) comparing the variable fluorescence of the unstressed plant with the variable fluorescence of the stressed plant to determine the susceptibility of the plant to a photoinhibitory stress.

11. The method of claim 10 wherein the level of transient fluorescence of the unstressed plant is measured within approximately 300 usec of the exposure of the unstressed plant to the flash of light and wherein the level of transient fluorescence of the stressed plant is measured within approximately 300 usec of the exposure of the stressed plant to the flash of light.

12. The method of claim 10 wherein the level of transient fluorescence of the unstressed plant is measured within approximately 200 usec of the exposure of the unstressed plant to the flash of light and wherein the level of transient fluorescence of the stressed plant is measured within approximately 200 usec of the exposure of the stressed plant to the flash of light.

13. The method of claim 10 wherein the level of transient fluorescence of the unstressed plant is measured at a point in time subsequent to the flash end point of the first flash of light and wherein the level of transient fluorescence of the stressed plant is measured at a point in time subsequent to the flash end point of the second flash of light.

14. The method of claim 10 wherein the first flash of light comprises a first series of flashes of light to bring about a first series of fluorescent transients; wherein the second flash of light comprises a second series of flashes of light to bring about a second series of fluorescent transients; wherein comparing the level of transient fluorescence of the unstressed plant with the steady state level of fluorescence of the unstressed plant comprises comparing and averaging each fluorescent transient in the first series of fluorescent transients with the steady state level of fluorescence of the unstressed plant; and, wherein comparing the level of transient fluorescence of the stressed plant with the steady state level of fluorescence of the stressed plant comprises comparing and averaging each fluorescent transient in the second series of fluorescent transients with the steady state level of fluorescence of the stressed plant.

15. The method of claim 14 wherein each of said first series of flashes and said second series of flashes comprises between about 10 and about 200 flashes.

16. The method of claim 10 wherein said determination of variable fluorescence of the unstressed plant further comprises comparison with the variable fluorescence of a control plant.

17. The method of claim 10 wherein the photoinhibitory stress is chilling stress.

18. A fluorimeter for measuring variable fluorescence of a plant comprising:

(a) a steady lamp to provide a source of steady light to bring about steady state fluorescence of a plant;

(b) a flash lamp to provide a flash of light to bring about transient fluorescence of the plant;

(c) a photosensor to receive steady state fluorescence and transient fluorescence from the plant and to provide an output signal proportional to the received fluorescence;

(d) fiber optics positioned with relation to the steady lamp and flash lamp to convey light from the steady lamp and the flash lamp to the plant;

(e) fiber optics positioned with relation to the photosensor to convey steady state fluorescence and transient fluorescence from the plant to the photosensor; and (f) electronic means electrically connected to the photosensor to receive the output signal from the photosensor and to measure and compare the level of steady state fluorescence and the level of transient fluorescence, wherein the level of transient fluorescence is measured within approximately 500 usec of the flash start point.

19. The fluorimeter of claim 18 wherein the level of transient fluorescence is measured within approximately 300 usec of the flash start point.

20. The fluorimeter of claim 18 wherein the level of transient fluorescence is measured within approximately 200 usec of the flash start point.

21. The fluorimeter of claim 18 wherein the level of transient fluorescence is measured at a point in time subsequent to the flash end point.

22. The fluorimeter of claim 18 wherein the flash lamp is capable of providing a series of flashes and wherein the electronic means is capable of measuring and comparing the level of steady state fluorescence with the level of transient fluorescence resulting from each flash in the series of flashes, and averaging the differences.

23. The fluorimeter of claim 18 wherein the electronic means comprises a current sensing amplifier, sample and hold current nulling circuitry, and sample and hold transient measurement circuitry.

* * * * *